United States Patent
Hahnen

[19]

[11] Patent Number: 5,549,605
[45] Date of Patent: Aug. 27, 1996

[54] ROLLER ELECTRODES FOR ELECTROCAUTERY PROBES FOR USE WITH A RESECTOSCOPE

[75] Inventor: Kevin F. Hahnen, Cooper City, Fla.

[73] Assignee: Symbiosis Corporation, Miami, Fla.

[21] Appl. No.: 425,367

[22] Filed: Apr. 20, 1995

[51] Int. Cl.[6] .................. A61B 17/32; A46B 17/39
[52] U.S. Cl. ....................... 606/46; 606/47; 606/48; 606/49
[58] Field of Search ................ 606/40, 41, 46, 606/47, 48, 49

[56] References Cited

U.S. PATENT DOCUMENTS

| | | |
|---|---|---|
| 1,971,024 | 8/1934 | Wappler . |
| 2,487,502 | 11/1949 | Willinsky . |
| 2,815,757 | 12/1957 | Piar . |
| 3,752,159 | 8/1973 | Wappler ........................... 606/46 |
| 4,917,082 | 4/1990 | Grossi et al. .................... 606/46 |
| 5,196,011 | 3/1993 | Korth et al. ..................... 606/46 |
| 5,324,288 | 6/1994 | Billings et al. .................. 606/45 |
| 5,354,296 | 10/1994 | Turkel ............................. 606/40 X |
| 5,395,312 | 3/1995 | Desai .............................. 604/22 |
| 5,395,363 | 3/1995 | Billings et al. ................. 606/48 X |

FOREIGN PATENT DOCUMENTS

WO81/03271  11/1981  WIPO .................................. 606/46

*Primary Examiner*—Angela D. Sykes
*Assistant Examiner*—Stephen D. Huane
*Attorney, Agent, or Firm*—David P. Gordon

[57] ABSTRACT

An electrocautery probe includes a pair of arms between which a roller electrode is mounted. The arms are joined at their proximal ends to an electrode lead and a mounting sleeve is provided intermediate of the arms and the lead for slideably coupling the probe to a resectoscope. According to the invention, the roller electrode is provided with a plurality of longitudinal surface grooves which increase surface area of the electrode and also enhance traction of the electrode. Other embodiments of the invention have eccentric convex or concave surfaces to further increase the surface area of the electrode. The electrodes according to the invention are preferably made of copper, chromium cobalt, or carbonless stainless steel. They preferably have an overall diameter of from about 0.115 to about 0.187 inches and an overall length of from about 0.110 to about 0.120 inches.

21 Claims, 5 Drawing Sheets

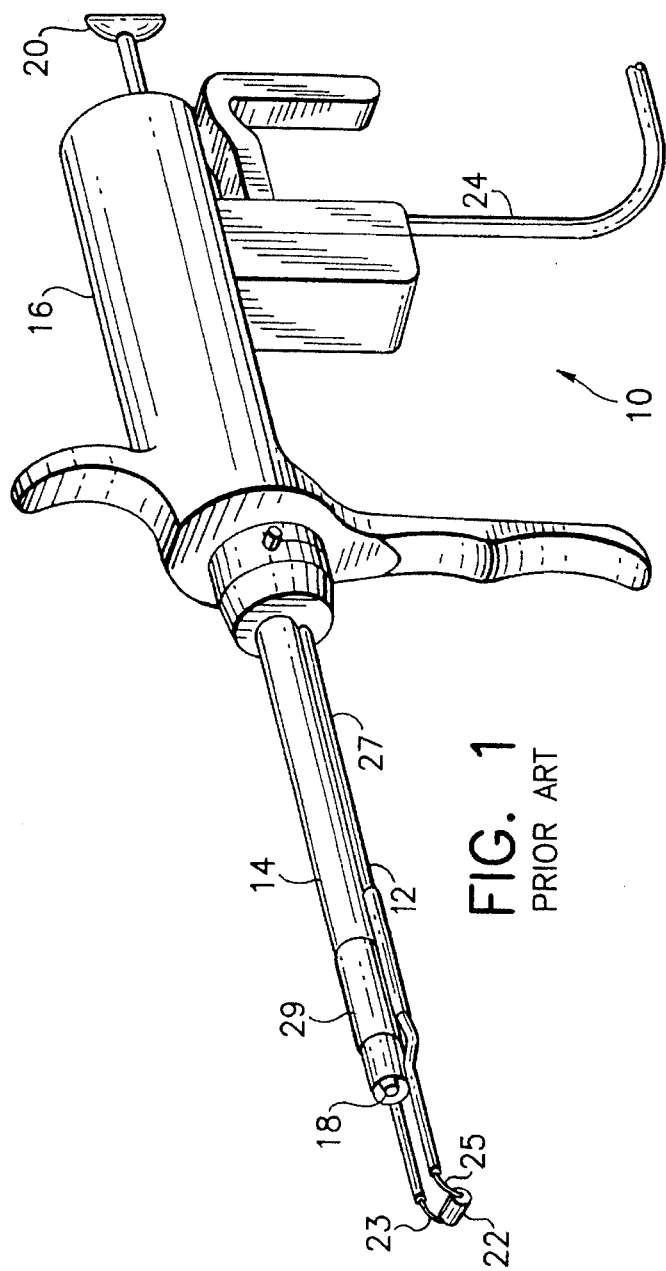
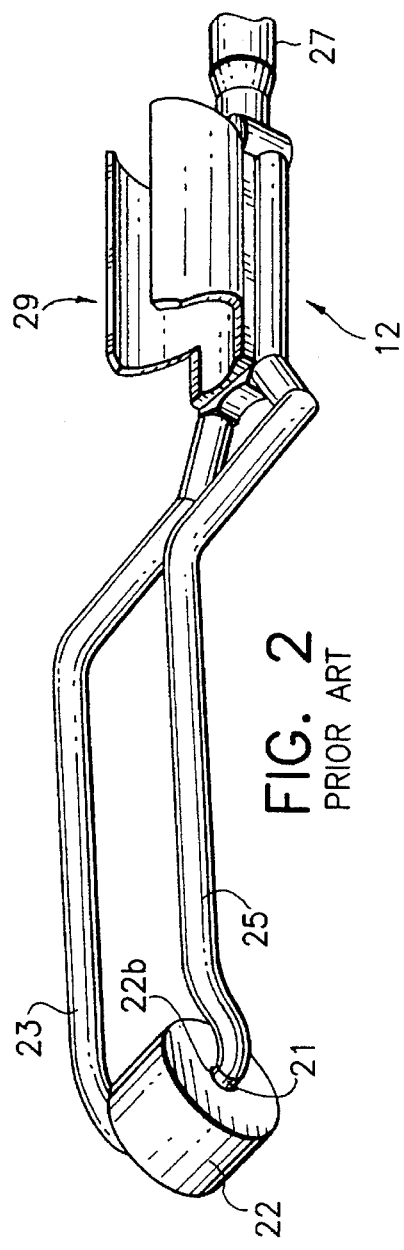
FIG. 1
PRIOR ART
FIG. 2
PRIOR ART

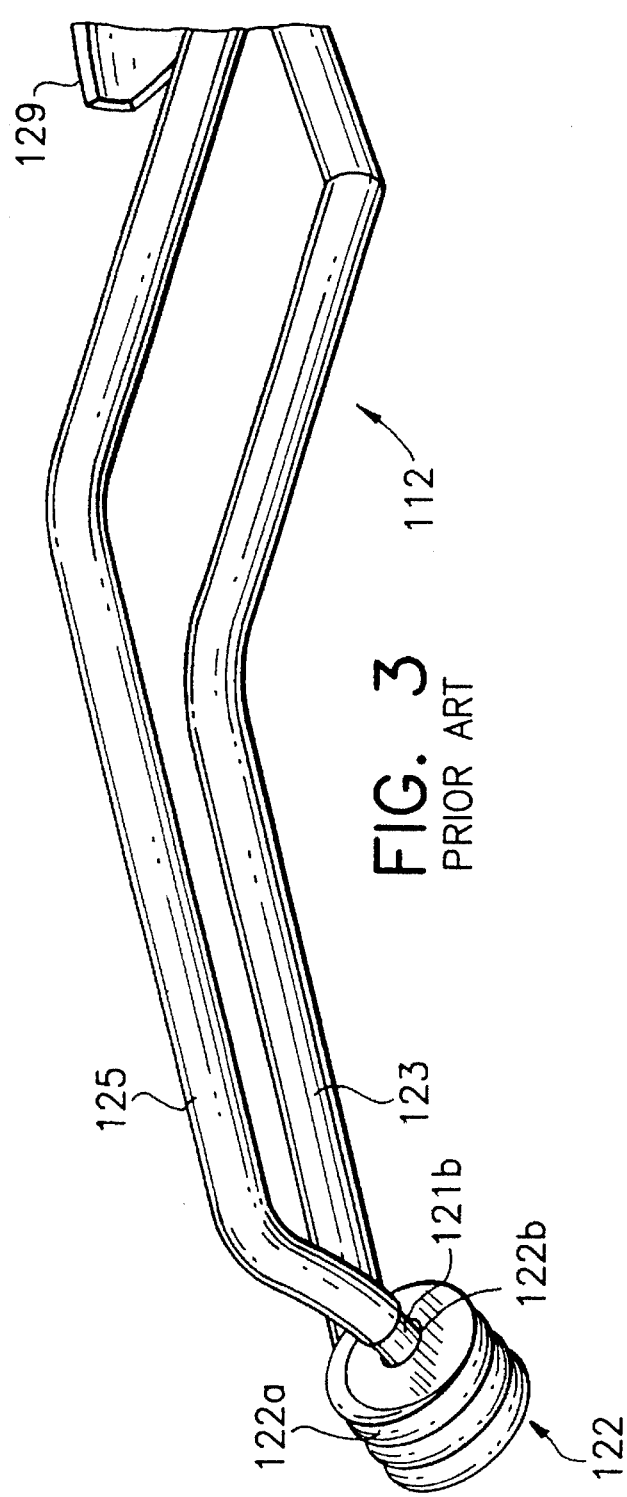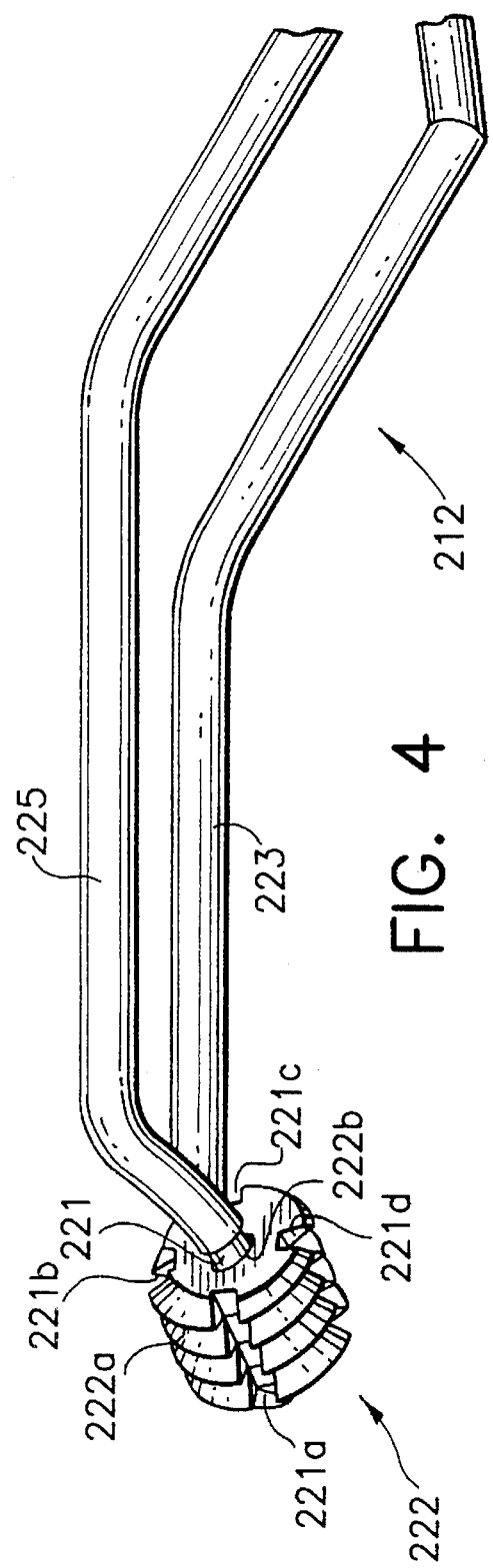

ROLLER ELECTRODES FOR ELECTROCAUTERY PROBES FOR USE WITH A RESECTOSCOPE

BACKGROUND OF THE INVENTION

1. Field of the Invention

The invention relates to endoscopic instruments. More particularly, the invention relates to electrocautery probes for use with a resectoscope or hysteroscope and specifically relates to roller electrodes used in electrocautery probes.

2. State of the Art

Electrosurgical resection is a procedure in which damaged or enlarged tissue is excised with an electrocautery probe. Transurethral resection is an electrosurgical procedure in which a portion of the prostrate is excised by means of an instrument passed through the urethra. Endometrial ablation is an electrosurgical alternative procedure to hysterectomy for women with menorrhagia (abnormal or excessive uterine bleeding). In these procedures, the instrument typically used is called a resectoscope or hysteroscope. Prior art FIG. 1 shows a typical resectoscope 10 with an electrocautery probe 12. The resectoscope 10 includes a distal guide tube 14 and a proximal handle 16. A telescope 18 is inserted through the guide tube 14 and is provided with a proximal eye piece 20 for viewing the interior of the bladder or other operative site. The cautery probe 12 has a distal electrode 22 which is mounted between a pair of arms 23, 25. The arms 23, 25 are joined at their proximal ends to an electrode lead 27 which is coupled via the handle 16 to a wire 24 which is coupled to a source of cautery current (not shown). A mounting sleeve 29 is provided on the probe 12 for slideably coupling it to the guide tube 14. The mounting sleeve 29 is typically located at the point where the arms 23, 25 are joined to the electrode lead 27. The handle 16 is generally capable of axially sliding the probe 12 and its distally mounted electrode 22 relative to the guide tube 14.

The ablation or resection procedure involves applying a cauterizing voltage to the electrode 22 and moving the electrode slowly over the prostate or endometrium while viewing the tissue through the scope 18. Thermal energy is applied through the electrode to the prostate or the endometrium so that tissue is excised. The resectoscope and cautery probe are also useful in other procedures for resecting the uterus, ureter, or renal pelvis.

Known electrodes for use in resectoscopes are available in many different shapes and sizes. U.S. Pat. No. 4,917,082 to Grossi et al., for example, discloses several embodiments of a "Resectoscope Electrode" including a coagulating electrode, a knife electrode, a punctate electrode, and a roller electrode, among others. Electrodes for use with resectoscopes are also widely available from Olsen Electrosurgical, Inc., Concord, Calif. They are available as blades, needles, balls, loops, spear tips, flexible wires, semi-circular wires, hooks, spatulas and blunt tips.

Recently, the generally preferred electrode for use in endometrial ablation is the roller (often referred to as "roller bar" or "roller ball") electrode. Prior art FIGS. 1 and 2 show a roller bar electrode 22. The roller bar is approximately 2.5 mm long and has a central bore 22b. It is rotatably mounted between the arms 23, 25 at the distal end of the electrocautery probe 12 by means of an axle wire 21 which extends through the central bore 22b of the electrode 22. The roller bar is supplied with a cauterizing voltage through the wire 21 which is coupled to the arms 23, 25 in the probe 12. When energized, the electrode 22 is rolled across the endometrial surface methodically until desired areas of the endometrium have been ablated. Roller bar electrodes are also used in prostatic resection. It is generally appreciated that in both endometrial ablation and prostatic resection, a larger surface area will allow the electrode to cover more tissue and thereby shorten the procedure. It is also understood that in the case of prostatic resection, the overall size of the electrode (as well as the resectoscope) must be kept to a minimum. Thus, it is difficult to increase the surface area of the electrode while maintaining a small overall size. One known way of providing increased electrode surface area while maintaining a small overall size is disclosed in co-owned U.S. Pat. No. 5,354,296 which describes a variable morphology electrode. Another way of providing increased electrode surface area while maintaining a small overall size is to provide radial or helical grooves in the surface of the roller bar. Prior art FIG. 3 shows an electrocautery probe 112 which is fitted with a roller electrode 122 having a helical groove 122a. The groove effectively increases the surface area of the electrode without increasing its overall size. However, the resulting roller electrode lacks traction and tends to glide over the tissue rather than rolling. This causes tissue to accumulate on the surface of the electrode and interfere with the surgical procedure.

SUMMARY OF THE INVENTION

It is therefore an object of the invention to provide an electrocautery probe having an electrode with a maximized surface area.

It is also an object of the invention to provide an electrocautery probe having an electrode with a relatively small overall size.

It is another object of the invention to provide an electrocautery probe having a roller electrode with enhanced traction.

It is still another object of the invention to provide an electrocautery probe having an electrode with a minimized mass.

It is another object of the invention to provide an electrocautery probe having an electrode with high heat zones for better tissue vaporization.

In accord with these objects which will be discussed in detail below, the electrocautery probe of the present invention includes a pair of arms between which a roller electrode is mounted. The arms are joined at their proximal ends to an electrode lead and a mounting sleeve is provided intermediate of the arms and the lead for slideably coupling the probe to a resectoscope. According to one aspect of the invention, the roller electrode is provided with a plurality of longitudinal surface grooves which increase surface area of the electrode and also enhance traction of the electrode. The grooves preferably have a depth of approximately 15–20% of the overall diameter of the roller electrode. According to another aspect of the invention, the electrode is provided with an eccentric concave or convex surface which increase the surface are of the electrode. The longitudinal grooves may also be provided on electrodes having an eccentric surface thereby providing both increased traction and increased surface area.

The electrodes according to the invention are preferably made of copper, chromium cobalt, or carbonless stainless steel. They preferably have an overall diameter of from about 0.115 to about 0.187 inches and an overall length of from about 0.110 to about 0.120 inches. It has been discovered that the relatively sharp edges defined by the surface grooves also provide high heat zones for enhanced tissue vaporization.

Additional objects and advantages of the invention will become apparent to those skilled in the art upon reference to the detailed description taken in conjunction with the provided figures.

BRIEF DESCRIPTION OF THE DRAWINGS

FIG. 1 is perspective view of a prior art resectoscope with an electrocautery probe having a roller bar electrode;

FIG. 2 is an enlarged broken perspective view of the distal end of the prior art electrocautery probe of FIG. 1;

FIG. 3 is an enlarged broken perspective view of the distal end of another prior art electrocautery probe having a roller electrode with a helical surface groove;

FIG. 4 is a view similar to FIG. 3 of the distal end of an electrocautery probe having a roller electrode with longitudinal grooves according to a first embodiment of the invention;

DETAILED DESCRIPTION OF THE PREFERRED EMBODIMENTS

Figure 5:
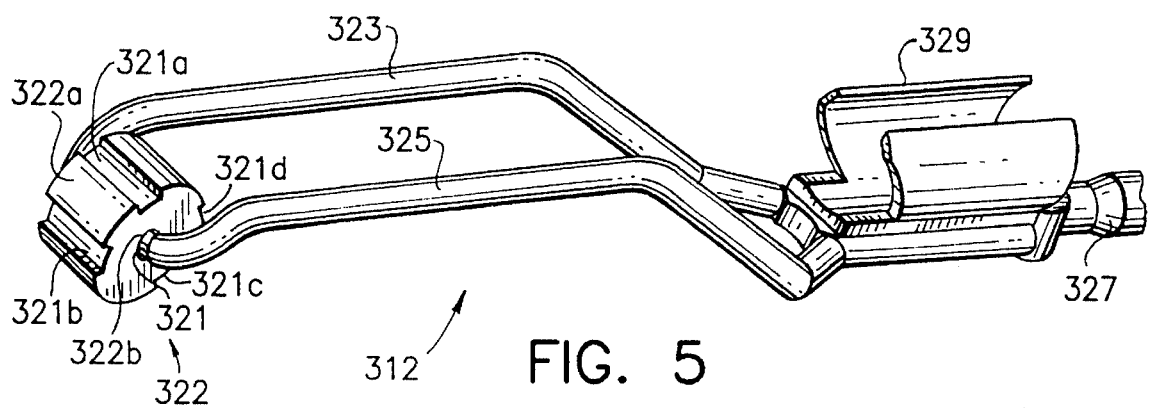
FIG. 5 is a view similar to FIG. 2 of an electrocautery probe having a roller electrode with longitudinal grooves according to a second embodiment of the invention.

Referring now to FIG. 4, an electrocautery probe 212 according to the invention includes an electrode 222 which is rotatably mounted between a pair of arms 223,225 at their distal ends. The proximal ends of the arms 223, 225 are coupled to an electrode lead and a mounting sleeve (not shown) in a conventional manner. The electrode 222 is a substantially cylindrical member having a helical surface groove 222a and a central axial bore 222b through which it is mounted to the arms 223, 225 in a conventional manner using an axle wire 221. The electrode may be made of copper, chromium cobalt, or carbonless stainless steel. It has an overall diameter of approximately 0.115–0.187 inches and a length of approximately 0.110–0.120 inches. The axial bore 222b has a diameter of approximately 0.020 inches and the axle wire 221 has a diameter of approximately 0.016 inches. According to the invention, a plurality of longitudinal surface grooves 221a–221d are provided on the outer surface of the electrode. The grooves are preferably approximately 0.020 inches deep, approximately 0.010 to 0.020 inches wide, and extend along substantially the entire length of the electrode. In the embodiment shown in FIG. 4, these grooves 221a–221d are spaced equidistantly about the electrode 222 and are substantially parallel to each other and to the rotational axis of the electrode. This arrangement places the longitudinal grooves 221a–221d substantially perpendicular to the helical groove 222a. The provided electrode has improved traction as compared to the prior art electrode shown in FIG. 3. In addition, the added longitudinal grooves 221a–221d increase the surface area of the electrode 222. Further, the relatively sharp portions of the electrode 222 defined by the helical and longitudinal grooves, serve as high heat zones for better tissue vaporization. It will be appreciated according to this embodiment of the invention, the helical groove 222a may be replaced with a plurality of parallel radial grooves and that the longitudinal grooves need not be parallel to each other or to the rotational axis of the electrode. As shown in FIG. 4, the helical groove has a V-shaped section and the longitudinal grooves have U-shaped sections. However, it will be appreciated that the grooves may have other shapes. While it is preferable that the longitudinal grooves extend along substantially the entire length of the electrode, it is sufficient that longitudinal grooves cross at least some of the radial grooves or at least a portion of the helical groove.

Turning now to FIG. 5, a second embodiment of an electrode 322 according to the invention is shown mounted on the distal end of a probe 312. The probe 312 is substantially the same as the probes 12, 112, and 212 described above, and similar reference numerals refer to similar parts of the probe. The electrode 322 is a substantially cylindrical member having a relatively smooth surface 322a and an axial bore 322b. The outer surface of the electrode 322 is provided with a plurality of longitudinal grooves 321a–321d. The electrode 322 may be made of the same materials and the same or similar dimensions as the electrode 222 described above. The provided electrode has increased traction due to the grooves 321a–321d and a somewhat increased surface area due to the grooves. In addition, it will be understood that the relatively sharp areas defined by the grooves provide high heat zones for better tissue vaporization.

Figure 6:
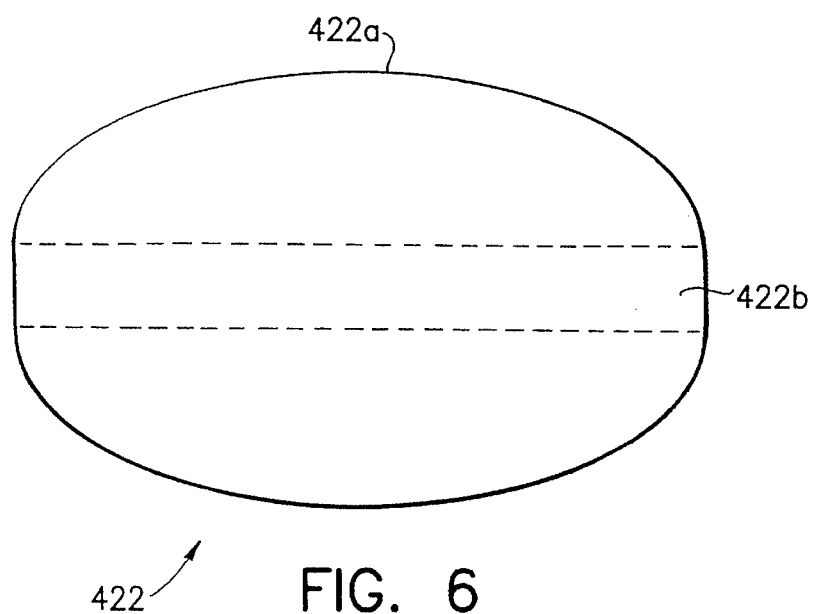
FIG. 6 is an enlarged side elevation view of a roller electrode with an eccentric surface according to a third embodiment of the invention.

Turning now to FIG. 6, a third embodiment of an electrode 422 is shown apart from a cautery probe. The electrode 422 has a convex eccentric surface 422a which is either ovoid or ellipsoid, and a longitudinal bore 422b for mounting it on a cautery probe (not shown). The eccentric surface 422a of the electrode 422 provides an increased surface area without dramatically increasing the overall size of the electrode.

Figure 7:
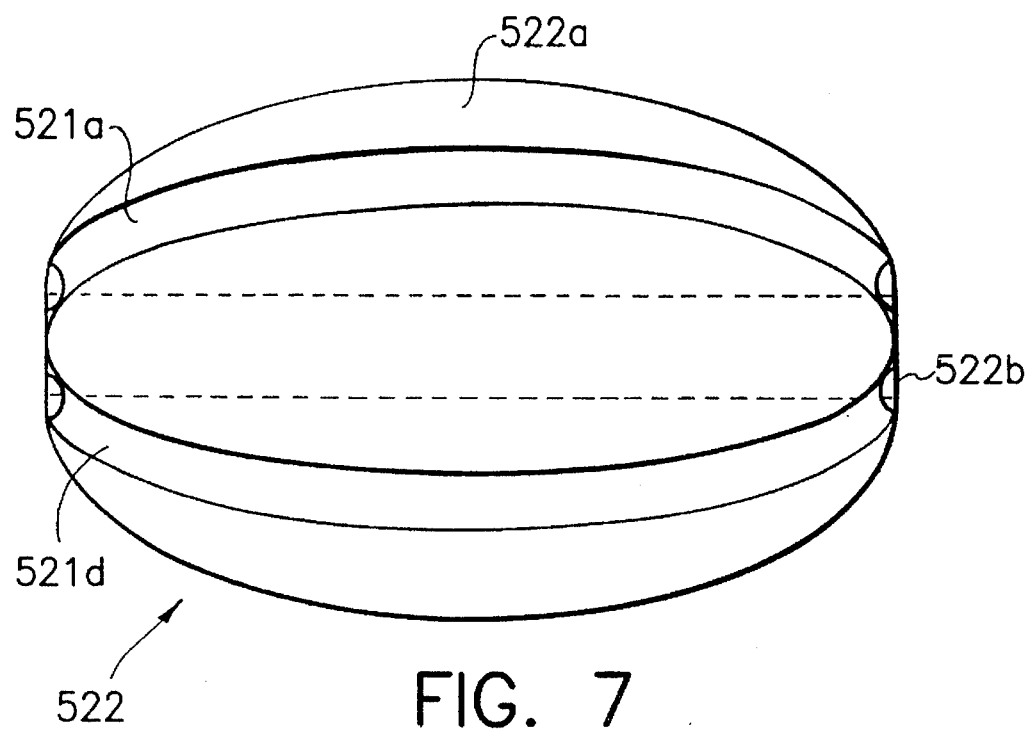
FIG. 7 is an enlarged side elevation view of a roller electrode with an eccentric surface and longitudinal grooves according to a fourth embodiment of the invention.

Turning now to FIG. 7, a fourth embodiment of an electrode 522 according to the invention has a substantially ovoid, ellipsoid or otherwise convex eccentric surface 522a and a longitudinal bore 522b for mounting it between arms of a probe (not shown) in a conventional manner. The outer surface of the electrode 522 is provided with a plurality of longitudinal grooves 521a–521d. The electrode 522 may be made of the same materials and the same or similar dimensions as the electrode 422 described above. The provided electrode has increased surface area due in part to its eccentric surface and also due in part to the grooves. It will be appreciated that, the grooves provide added traction for the electrode when it is mounted for rotation at the distal end of a cautery probe. In addition, it will be understood that the grooves define relatively sharp edges which serve as high heat zones for better tissue vaporization.

Figure 8:
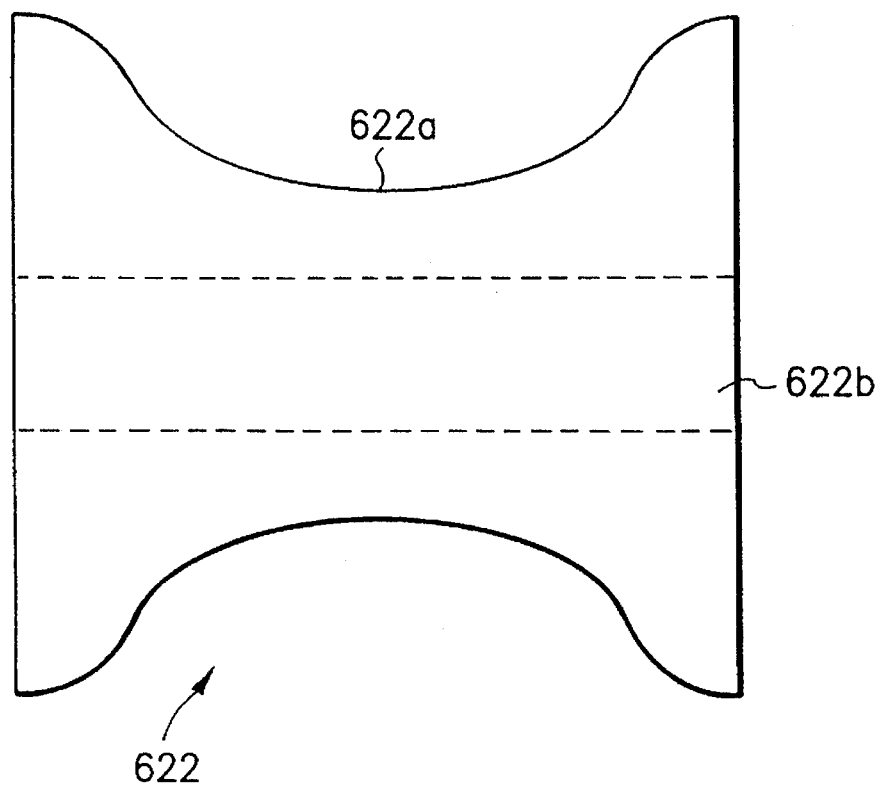
FIG. 8 is an enlarged side elevation view of a roller electrode with an eccentric surface according to a fifth embodiment of the invention.

A fifth embodiment of the invention is shown in FIG. 8. The electrode 622 shown in FIG. 8 has a concave eccentric surface 622a and resembles a spool. An axial bore 622b is provided for mounting the electrode between arms (not shown) in a conventional manner. The electrode 622 may be made of the same materials and similar dimensions as the electrode 222 described above. The provided electrode has an enlarged surface area and reduced mass. The electrode will therefore heat up faster.

Figure 9:
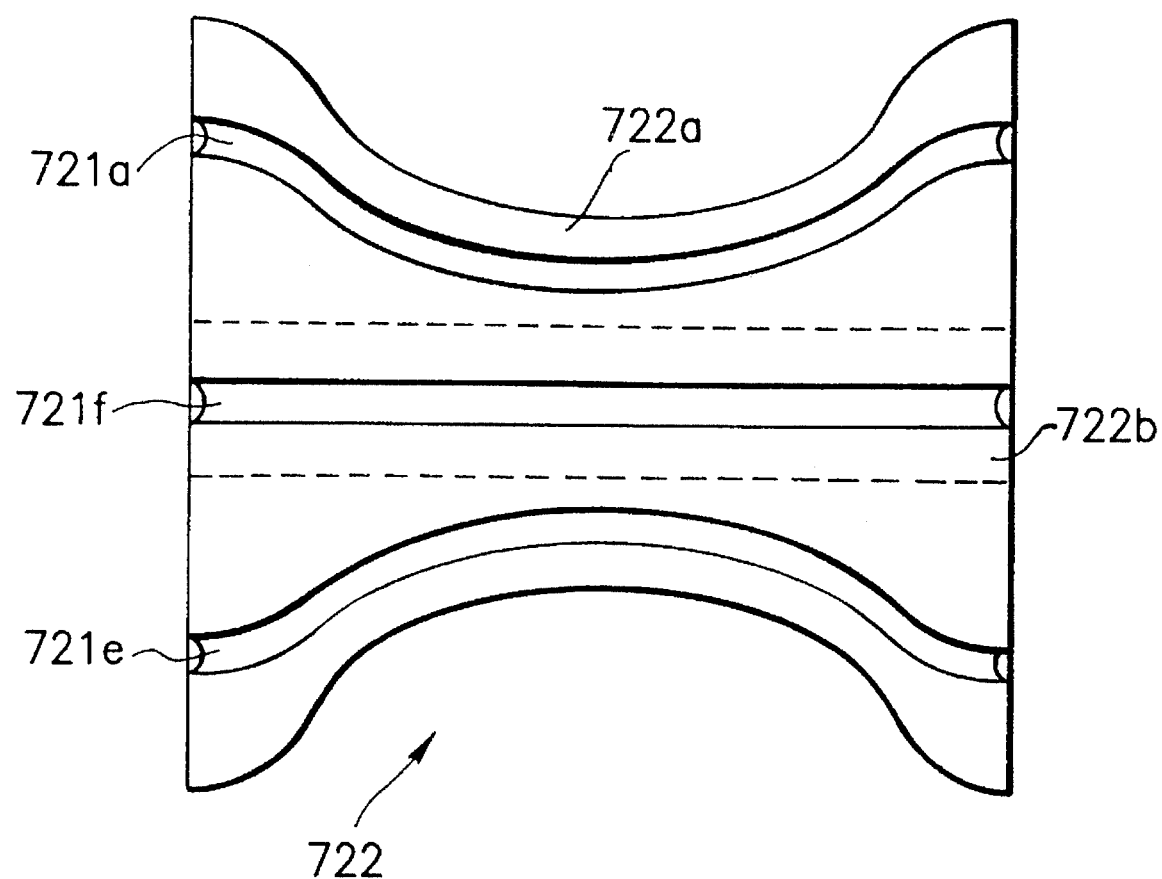
FIG. 9 is an enlarged side elevation view of a roller electrode with an eccentric surface and longitudinal grooves according to a sixth embodiment of the invention.

FIG. 9 shows a sixth embodiment of the invention. The electrode 722 shown in FIG. 9 is similar to the electrode 622 described above with a concave eccentric surface 722a and an axial bore 722b. The electrode 722 is also provided with a plurality of longitudinal grooves 721a–721f. The grooves provide increased traction to keep the electrode rolling when it is moved over tissue and also provide additional high heat zones as described above. From the foregoing, it will also be understood that it may be advantageous to place the grooves only at the extreme ends of the electrode, i.e. on the high points of the spool. This would be advantageous, for example, where the waist portion of the spool is too thin to be provided with a groove.

There have been described and illustrated herein several embodiments of electrocautery probes for use with a resectoscope. While particular embodiments of the invention have been described, it is not intended that the invention be limited thereto, as it is intended that the invention be as broad in scope as the art will allow and that the specification be read likewise. Thus, while particular dimensions and materials have been disclosed, it will be appreciated that other dimensions and materials could be utilized. Also, while parallel longitudinal grooves have been shown, it will be recognized that other types of longitudinal grooves could be used with similar results obtained. Moreover, while particular configurations have been disclosed in reference to features of the cautery probe carrying the electrode, it will be appreciated that other configurations of a cautery probe could be used with the provided electrodes. Furthermore, while the probes and electrodes have been disclosed as having particular utility in conjunction with a resectoscope, it will be understood that the cautery probes and electrodes disclosed herein can be used in other surgical procedures without requiring a resectoscope. It will therefore be appreciated by those skilled in the art that yet other modifications could be made to the provided invention without deviating from its spirit and scope as so claimed.

What is claimed is:

1. A roller electrode for use in an electrocautery probe having two arms between which said electrode is mounted for rotation, said electrode comprising:

a conductive member having an inner axial bore defining an axis of rotation and an outer surface, said outer surface having at least one radial groove which is substantially perpendicular to said axis of rotation.

2. A roller electrode according to claim 1, wherein:

said outer surface has a plurality of radial grooves, each of which is substantially perpendicular to said axis of rotation.

3. A roller electrode according to claim 1, wherein:

said conductive member is substantially cylindrical.

4. A roller electrode according to claim 2, wherein:

said conductive member is substantially cylindrical.

5. A roller electrode according to claim 1, wherein:

said outer surface has at least one longitudinal groove which is substantially perpendicular to said at least one radial groove.

6. A roller electrode according to claim 2, wherein:

said outer surface has at least one longitudinal groove which is substantially perpendicular to said at least one radial groove.

7. A roller electrode according to claim 3, wherein:

said outer surface has at least one longitudinal groove which is substantially perpendicular to said at least one radial groove.

8. A roller electrode according to claim 4, wherein:

said outer surface has at least one longitudinal groove which is substantially perpendicular to said at least one radial groove.

9. A roller electrode according to claim 1, wherein:

said conductive member is made of one of copper, chromium cobalt, and carbonless stainless steel.

10. A roller electrode according to claim 1, wherein:

said conductive member has an overall diameter of approximately 0.115–0.187 inches and a length of approximately 0.110–0.120 inches.

11. An electrocautery probe, comprising:

a) a pair of conductive arms having proximal and distal ends, said arms being joined to each other at their proximal ends;

b) an electrode lead coupled to said proximal ends of said conductive arms and extending proximally therefrom;

c) a roller electrode mounted between said distal ends of said conductive arms, said roller electrode comprising a conductive member having an inner axial bore defining an axis of rotation and an outer surface, said outer surface having at least one longitudinal groove which is substantially parallel to said axis of rotation; and d) means for coupling said probe to a resectoscope.

12. An electrocautery probe according to claim 11, wherein:

said outer surface has a plurality of longitudinal grooves, each of which is substantially parallel to said axis of rotation.

13. An electrocautery probe according to claim 11, wherein:

said conductive member is substantially cylindrical.

14. An electrocautery probe according to claim 12, wherein:

said conductive member is substantially cylindrical.

15. An electrocautery probe according to claim 11, wherein:

said outer surface has at least one radial groove which is substantially perpendicular to said at least one longitudinal groove.

16. An electrocautery probe according to claim 12, wherein:

said outer surface has at least one radial groove which is substantially perpendicular to said at least one longitudinal groove.

17. An electrocautery probe according to claim 13, wherein:

said outer surface has at least one radial groove which is substantially perpendicular to said at least one longitudinal groove.

18. An electrocautery probe according to claim 14, wherein:

said outer surface has at least one radial groove which is substantially perpendicular to said at least one longitudinal groove.

19. An electrocautery probe according to claim 11, wherein:

said conductive member is made of one of copper, chromium cobalt, and carbonless stainless steel.

20. An electrocautery probe according to claim 11, wherein:

said conductive member has an overall diameter of approximately 0.115–0.187 inches and a length of approximately 0.110–0.120 inches.

21. An electrocautery probe according to claim 11, wherein:

said means for coupling comprises a mounting sleeve for sildeably coupling said probe to the resectoscope.

* * * * *